(12) United States Patent
Niklasson et al.

(10) Patent No.: US 7,803,525 B2
(45) Date of Patent: Sep. 28, 2010

(54) DETECTION METHOD FOR LJUNGAN VIRUS

(75) Inventors: Bo Niklasson, Kalmar (SE); Andreas Nitsche, Berlin (DE); Oliver Donoso Mantke, Berlin (DE); Matthias Niedrig, Berlin (DE)

(73) Assignees: Apodemus AB, Kalmar (SE); Robert-Koch Institut, Berlin (DE)

( * ) Notice: Subject to any disclaimer, the term of this patent is extended or adjusted under 35 U.S.C. 154(b) by 87 days.

(21) Appl. No.: 11/817,984

(22) PCT Filed: Mar. 15, 2006

(86) PCT No.: PCT/GB2006/000926

§ 371 (c)(1),
(2), (4) Date: May 14, 2008

(87) PCT Pub. No.: WO2006/009772

PCT Pub. Date: Sep. 21, 2006

(65) Prior Publication Data

US 2009/0155769 A1 Jun. 18, 2009

(30) Foreign Application Priority Data

Mar. 15, 2005 (GB) .................. 0505321.0

(51) Int. Cl.
*C12Q 1/70* (2006.01)
*C12Q 1/68* (2006.01)
*C07H 21/00* (2006.01)
(52) U.S. Cl. .............. 435/5; 435/6; 536/24.32
(58) Field of Classification Search ............ None
See application file for complete search history.

(56) References Cited

FOREIGN PATENT DOCUMENTS

WO    WO 03019197    *  3/2003

OTHER PUBLICATIONS

Johansson et al (Journal of Virology 76: 8920-8930, 2002).*
Niklasson et al (Ann. N. Y. Acad Sci 1005: 170-175, 2003).*
Nitsche et al (Clinical Chemistry 45 (11): 1932-1937, 1999).*
Buck et al (BioTechniques 27:528-536, 1999).*

* cited by examiner

*Primary Examiner*—Mary E Mosher
(74) *Attorney, Agent, or Firm*—Kohn & Associates, PLLC

(57) ABSTRACT

The present invention relates to a method for specifically detecting Ljungan virus (LV). In particular, the present invention relates to a method of detecting LV using quantitative real-time reverse transcriptase PCR. The present invention also provides kits for performing the method of the invention.

27 Claims, 3 Drawing Sheets

DETECTION METHOD FOR LJUNGAN VIRUS

CROSS-REFERENCE TO RELATED APPLICATIONS

This is a National Phase Filing Under 35 U.S.C. 371, of International Application No. PCT/GB06/000926, filed 15 Mar. 2006, which claims priority to Great Britain Patent Application Ser. No. 0505321.0, filed 15 Mar. 2005, both of which are incorporated herein by reference.

TECHNICAL FIELD

The present invention relates to a method for specifically detecting Ljungan virus (LV). In particular, the present invention relates to a method of detecting LV using quantitative real-time reverse transcriptase PCR. The present invention also provides kits for performing the method of the invention.

BACKGROUND OF THE INVENTION

LV belongs to the Picornavirus family and is therefore an RNA virus. LV was first identified in bank voles (*Clethrionomys glareolus*) and is known to cause disease in a number of animals. Three isolates of the virus (87-012, 174F and 145SL) were disclosed in International Patent Application WO 98/11133 and the partial sequence of each isolate disclosed therein. The full sequences of the three LV's were subsequently published (Johansson et al., J. Virol., 76, 8920-8930, 2002).

Comparative sequence analysis of the LV prototype strain, 87-012, and two other serologically related LV isolates, 174F and 145SL, revealed that the genomes of these newly determined Swedish LV strains are closely related and possess the following deviant picornavirus-like organization (Johansson et al., 2002, supra):

```
5'UTR-VP0-VP3-VP1-2A1-2A2-2B-2C-3A-3B-3C-3D-3'UTR.
```

Phylogenetic analysis showed that the LV isolates constitute a distinct monophyletic group, which, together with the genus *Parechovirus*, is separated from other members of the Picornaviridae (Johansson et al., 2002, supra; Lindberg and Johansson, Virus Res., 85, 61-70, 2002). Furthermore, a complete genomic sequence of another virus, M1146, which was isolated from another vole species (*Microtus montanus*), trapped in Oregon, USA, verified that this virus is also a member of the Picornaviridae, most closely related to the LVs isolated in Sweden and is a new genotype within the distinct LV cluster (Johansson et al., J. Gen. Virol., 84, 837-844, 2003).

LV has been found in humans and can cause a variety of diseases. The identification of LV in Swedish and North American voles suggests a continuous presence of LV over a wide geographical range throughout numerous vole populations. Presently, there exist seven known strains of LV, namely 87-012 (NC 003976; AF327920), 174F (AF327921), 145SL (AF327922) and 342SL (B. Niklasson, unpublished data) originated from Sweden, and M1146 (AF538689), NY64-7855 (unpublished data) and NY64-7947 (unpublished data) originated from the USA. NCBI Genbank accession numbers or other sources are shown in brackets.

Genetically the LV genome and the encoded polyproteins exhibit several exceptional features, such as the absence of a predicted maturation cleavage of VP0, a conserved sequence determinant in VP0 that is typically found in VP1 of other Picornaviruses, and a cluster of two unrelated 2A proteins, namely 2A1 and 2A2 (Johansson et al., 2002, supra). The 2A1 protein is related to the 2A protein of cardio-, erbo-, tescho- and aphthoviruses and the 2A2 protein is related to the 2A protein of parechoviruses, kobuviruses and avian encephalomyelitis virus (Johansson et al., 2002, supra; Lindberg and Johansson, Virus Research, 85, 61-70, 2002).

LV is characterised by a chronic or long lasting infection in its rodent host and reservoir. LV infects different species of animals as well as humans and the infection may result in a long lasting or chronic infection. LV replicates in a wide variety of tissue culture cells giving a chronic infection with discrete cytopathogenic effect (CPE) and low viral output (in the order of 1000-100 000 viral particles per ml supernatant).

Data generated by virus cultivation under laboratory conditions show that LV grows/replicates in a number of cell lines that originate from different tissues and different species, e.g. Vero monkey kidney; Vero E6 monkey kidney; MA-104 monkey kidney; CV-1 monkey kidney; GMK monkey kidney; A-549 human lung; Hela human cervical tissue; BHK 21 hamster kidney; RD human muscle; and L-cells mouse skin.

In animals and humans, LV replicates in muscle tissue, including heart tissue, in neural cell, including the brain, and in endocrine glands, including the beta cells of the pancreas, the thyroid gland and the supra renal gland.

Data generated by detection of virus using LV specific immunohistochemistry tests and thin section electron microscopy in humans, bank voles, lemmings, laboratory mice rabbits, guinea pigs, arctic foxes and moose show that LV has been found in endocrine and exocrine pancreas tissue, in endothelial cells of vessels, cells in the brain (including nerve tissue), cells of the liver, cells of the placenta and the umbilical cord, muscle tissue, heart tissue and tissue of the thyroid gland (Niklasson et al., Ann NY Acad Sci, 1005, 170-175, 2003; and unpublished data).

It can therefore be concluded that LV can grow in most cell types of the body and therefore infect all organs of the body.

The most closely related animal viruses to LV are viruses in the cardiovirus genus.

Similarities

Cardioviruses belong to the picornavirus family.

Cardiovirus have rodents as their natural reservoir.

Cardioviruses can cause disease in a wide variety of animal species.

Cardiovirus can infect and cause disease in the same organs as LV.

Differences

Cardiovirus and LV are genetically distantly related.

The double 2 A of LV is absent in cardiovirus.

Cardiovirus is not related to LV by serology.

Cardiovirus cause an acute disease (not long lasting or chronic) when it affects its non-rodent victims.

Cardiovirus is easy to cultivate in tissue culture without adaptation while LV is often impossible to cultivate without blind passage in tissue culture or first passage in suckling mice and after several passages in suckling mice adaptation in tissue culture (see Johansson et al., BBRC, 317, 1023-1029, 2004).

Cardioviruses generally do not infect humans (only rare case reports in the literature e.g., Zimmerman, Encephalomyocarditis, In Handbook: Series of Zoonoses, G. B. Beran (Ed.), CRC Press Inc., Boca Raton, Fla., USA, 1994; and Tesh, Am. J. Trop. Med. Hyg., 27, 144-149, 1978).

It is likely that new variants of LV in different continents will be identified. As LVs are associated with a number of disease conditions it is desirable to have a simple efficient and effective test for detecting LVs. The test will need to be specific so that only LVs are detected and not other picornaviruses. Furthermore, it is desirable that the test can be used to detect all LVs strains, is highly specific and highly sensitive. It is also desirable that the test allows the quantitative measurement of LV so that the viral load can be determined.

In International Patent Application WO 2004/073710, the use of an antiviral agent to treat disease caused by LV infections is disclosed. By being able to test for the presence of LV the effectiveness of such treatments can be monitored, especially if the test is quantitative.

The current tests for the presence of LV are either very laborious, e.g., virus culture/isolation and detection of CPE, or not sensitive enough, e.g., immunohistochemistry tests, which do not detect all LVs or do not distinguish effectively between LVs and other picornaviruses.

There is therefore a need for a simple effective test for specifically detecting LV.

SUMMARY OF THE INVENTION

The present invention provides a method for detecting LV comprising detecting a nucleic acid sequence comprising at least 13 contiguous nucleotides of the sequence:

```
CTGCRYAGGTGGCTTTCACCTCTSGACAGYGC.  (SEQ ID NO. 1)
```

The method was designed to detect specifically all LV. By detecting the presence of at least 13 contiguous nucleotides of SEQ ID NO.1 or its reverse complement, all LVs can be specifically detected. In particular, the method does not detect non-Ljungan picornaviruses.

SEQ ID NO. 1 is present in the 5'UTR of LVs and is conserved in all known LV strains. The sequence is sufficiently different from the corresponding sequence in other non-Ljungan picornaviruses to ensure that only LVs are detected.

The term LV is as defined above and preferably means a picornavirus that encodes two unrelated 2A proteins in its genome. Methods for determining whether a virus encodes two unrelated 2A proteins are described in Lindberg et al., Virus Res., 85, 61-70, 2002. The term LV includes all the currently known LVs as well as LVs that are to be identified subsequently. Methods for identifying new LVs are described in International Patent Application WO 2004/073710.

The nucleic acid sequence to be detected can be a DNA or an RNA sequence. As would be apparent to one skilled in the art, if an RNA sequence was being detected, the Thymidine nucleotides in the sequence will be Uracil nucleotides. Preferably a cDNA sequence is detected. As discussed further below, LV RNA can be reverse transcribed into cDNA by using a reverse transcriptase.

Depending on which nucleic acid is being detected, the reverse complement of SEQ ID NO. 1 may alternatively be detected using the method of the present invention.

The reverse complement of SEQ ID NO. 1 is:

```
GCRCTGTCSAGAGGTGAAAGCCACCTRYGCAG.  (SEQ ID NO. 2)
```

The nucleic acid sequence being detected comprises at least 13 contiguous nucleotides of SEQ ID NO. 1 or its reverse complement. Preferably the nucleic acid sequence being detected comprises at least 15 contiguous nucleotides, more preferably at least 17 contiguous nucleotides. It is particularly preferred that the nucleic acid sequence being detected comprises the following sequence:

```
GCTTTCACCTCTSGACA        (SEQ ID NO. 3)
``` or its reverse complement.

The reverse complement of SEQ ID NO. 3 is:

```
TGTCSAGAGGTGAAAGC.       (SEQ ID NO. 4)
```

In the nucleotide sequences of the present invention and in accordance with standard nomenclature; R is A or G, Y is C or T, and S is G or C. The minor variations introduced into the sequences by the use of these terms are required in order to ensure that all LV's will be detected by the method of the present invention.

The nucleic acid sequence can be detected using any suitable technique. Preferably the nucleic acid sequence is detected by using one or more probes that specifically bind to the nucleic acid sequence. More than one probe can be used especially when the nucleic acid sequence being detected can vary in sequence. For example, when the nucleic acid sequence being detected comprises SEQ ID NO. 3, it is preferred that 2 probes are used. The first probe specifically anneals to GCTTTCACCTCTGGACA (SEQ ID NO. 5) and the second probe specifically anneals to GCTTTCACCTCTCGACA (SEQ ID NO. 6) so that both versions of the sequence can be detected. Preferably the first probe has the sequence TGTCCAGAGGTGAAAGC (SEQ ID NO. 7) and the second probe has the sequence TGTCGAGAGGTGAAAGC (SEQ ID NO. 8). Alternatively, one probe can be used which is capable of annealing to both SEQ ID NO. 5 and 6. It is known that there are polymorphisms in SEQ ID NO. 1 which can be used to distinguish LV isolates. For example, residue number 24 in SEQ ID NO. 1 is G for the Swedish LV isolates but C for the American LV isolates. By differentially labelling probes to the different sequences, it would be possible to determine which type of LV was present or even the ratio between the types of isolates.

Preferably the one or more probes are nucleic acid probes (oligoprobes) having the complementary sequence to that being detected. The term "complementary sequence" means a sequence in which substantially all (preferably all) nucleotide bases are able to form base pairs with the nucleotide bases in the nucleic acid sequence being detected. The probe may be of any suitable size but is preferably less than 25 nucleotides in length, more preferably less than 20 nucleotides in length and most preferably 17 nucleotides or less in length.

It is particularly preferred that the probe binds in the minor groove of the nucleic acid being detected by using suitable polycyclic reagents. By binding in the minor groove, the melting temperature of the probe increases making it possible to design relatively short probes (less than 25 nucleotides in length). Due to the similarity in sequence between LVs and other picornaviruses, it is desirable to use a relatively short probe so that unique sequences of LV can be detected.

Probes may be single or double stranded DNA or RNA including plus-sense RNA probes, minus-sense RNA probes, and antisense RNA probes.

Suitable labels for nucleic acids include radioactive and non-radioactive labels e.g. fluorescence, indirect detection systems and chemiluminescence.

Nucleic acids may be labelled using techniques such as those described in standard laboratory manuals (e.g., Sambrook et al., Molecular Cloning: A Laboratory Manual, New York: Cold Spring Harbor, 1989 or Current Protocols in Molecular Biology (Ausubel, F. M., regularly updated)) or using one of the large number of commercially available kits such as those provided by Promega (Southampton, Hampshire, UK), Roche (Lewes, East Sussex, UK), Ambion (Huntingdon, Cambridgeshire, UK) and BD Biosciences/Clontech (San Jose, Calif., USA).

Radioactive labels include $^{32}P$, $^{33}P$, $^{35}S$, $^{125}I$, $^{3}H$ or any other radioisotope. Nucleic acids may be radio-labelled using one of many methods known to the skilled man including 5'-end labelling, 3'-end labelling, nick translation and random primer labelling using for example random hexamers or random octamers.

Fluorescent labels include fluorescein, Cy5, Cy5.5 and FAM (6-carboxyfluorescein) or any other fluorescent dye, e.g. TET (tetrachloro-6-carboxyfluorescein), JOE (2,7-dimethyloxy-4,5-dichloro-6-carboxyfluorescein), and HEX (hexchloro-6-carboxy fluorescein).

Dendrimer-based labelling systems exist. This method of labelling uses a dendrimer to attach 200 or more fluorescent labels allowing the detection of a small number of target molecules. Such dendrimer technology is produced, for example, by Genisphere, Bala, Cynwyd, Pa., USA.

Alternatively, known particulate labels such as nano particles manufactured under the name "Quantum Dots" or "Luminex Beads" may be applied. Quantum Dots may be obtained, for example, from Quantum Dot Corporation, Hayward, Calif., USA.

WO 00/18965 discloses methods directed to the detection of the presence of mutations or polymorphisms. In particular, the polymerase chain reaction (PCR) and fluorescently labelled oligonucleotide hybridization probes are used to identify mutations and polymorphisms based on melting curve analysis of the hybridization probes. The fluorophores used are one of a number of different compounds known in the art to be suitable, including ethidium bromide, YO-PRO-1 and SYBR Green I.

Fluorescent resonance energy transfer (FRET) relies on the adjacent annealing of two hybridization probes (Lay and Wittwer, Clin. Chem., 43, 2262-2267, 1997). The first probe contains a donor dye at its 3' end, and the other contains an acceptor dye at its 5' end. When light is added through an external source, the donor dye is excited and transfers energy to the acceptor dye in the fluorescent resonance energy transfer process. Only when both probes anneal in close proximity, is energy transfer possible. Hence, such techniques allow the detection of the binding of complementary probes to specific sequences.

Another detection system comprises using exonuclease probes. Such probes comprise a reporter and a quencher dye, wherein the quencher prevents any signal from the reporter. The probes are used in methods wherein a region containing the target sequence is amplified by PCR. The probe binds to the desired target site and when the polymerase runs into the probe it treats the probe as an obstacle and removes it by cleaving it into pieces. The quencher is then separated from the reporter and the reporter can be detected.

Indirect detection systems comprise the incorporation of hapten-modified nucleotides into a probe molecule either by internal incorporation, end-labelling or chemical modification. Examples of haptens include: digoxigenin, biotin, sulfonated bases and dinitrophenol. Haptens, once incorporated into the probe, are detected with an affinity ligand covalently coupled to a signalling enzyme such as alkaline phosphatase. Commonly used ligands include streptavidin, avidin and antibodies (monoclonal and polyclonal). Alternatively, a nucleic acid intercalating moiety, psoralen, covalently attached to biotin can be used. The psoralen-biotin intercalates within the nucleic acid (single—or double-stranded) and is then covalently bound by irradiation with long-wave UV light.

Direct detection methods employ direct covalent attachment of the signalling enzyme to the nucleic acid probe, typically a synthetic oligonucleotide. This direct attachment eliminates the need to add a secondary reagent, reducing the number of detection steps and signal to noise problems. The signalling enzyme, e.g. biotin, can be incorporated into the nucleic acid probe directly by enzymatic polymerization with a biotinylated primer or by polymerization in the presence of biotinylated nucleotide triphosphates.

Fucose labelling systems may be used to couple haptens, fluorochromes or affinity ligands to any nucleic acid by attaching a universal, photo- or heat-activatable moiety to which any sulfhydryl-reactive compound can be linked. Fucose labelling kits, such as The FastTag Nucleic Acid Labelling System, are available from Vector Laboratories, Inc., Burlingame, Calif., USA.

Preferably the probe is a single stranded DNA probe.

As LV is an RNA virus it is preferred that reverse transcription is performed prior to detecting the nucleic acid sequence. Reverse transcription is a standard technique well known to those skilled in the art. A DNA primer is annealed to the RNA sequence and the primer extended by the action of the reverse transcriptase. The sequence of the primer must be complementary to the RNA sequence. The primer must anneal to the RNA sequence at a position enabling the production of a cDNA sequence comprising at least 13 contiguous nucleotides of SEQ ID NO. 1. Those skilled in the art can easily determine suitable primers enabling the production of such a DNA sequence.

Preferably the primer anneals to a conserved sequence of LV close to SEQ ID NO. 1, for example, within 200 nucleotides of SEQ ID NO. 1. By annealing to a conserved sequence of LV, the specificity of method is further improved.

In a particularly preferred embodiment, a primer comprising the sequence GCCCAGAGGCTAGTGTTACCA (SEQ ID NO. 9) is used to reverse transcribe Ljungan viral RNA.

By reverse transcribing Ljungan viral RNA the method of detection is improved as the specificity of the primer annealing to the viral RNA increases the level of specificity. Not only must the viral RNA have a complementary sequence to the primer but the reverse transcribed DNA sequence must comprise at least 13 contiguous nucleotides of SEQ ID NO. 1.

It is particularly preferred that the method of the present invention comprises:
(a) reverse transcribing LV RNA so that a DNA sequence is obtained that comprises at least 13 contiguous nucleotides of SEQ ID NO.1;
(b) amplifying the DNA sequence; and
(c) detecting the presence of the amplified DNA sequence.

As indicated above, the amplified DNA sequence can be detected by any known method. Preferably the amplified DNA sequence is detected by using a probe.

The LV RNA can be any RNA provided that on being reverse transcribed a DNA sequence is obtained that comprises at least 13 contiguous nucleotides of SEQ ID NO.1. The LV RNA can be reverse transcribed as described above.

The DNA sequence obtained by reverse transcription can be amplified by any suitable method. Preferably the DNA sequence is amplified by the polymerase chain reaction (PCR). Any suitable primers can be used in the PCR reaction to amplify a DNA sequence comprising at least 13 contiguous nucleotides of SEQ ID NO.1.

In order to increase the specificity of the claimed method, it is preferred that the primers used to amplify the DNA sequence comprising at least 13 contiguous nucleotides of SEQ ID NO.1 are chosen so that only DNA reverse transcribed from LV RNA is amplified and not RNA or DNA derived from another virus. The distance between the primers will depend on the limitation of the Taq polymerase used to amplify the DNA sequence. Preferably the primers used to amplify the DNA sequence are less than 200 nucleotides apart.

Preferably the primers used to amplify the DNA sequence comprising at least 13 contiguous nucleotides of SEQ ID NO.1 comprise:

a forwards primer having the sequence TAGGGGCTGTAC-CCGGGCGGTCCCACTCTTCACAG (SEQ ID NO. 10) or at least 13 contiguous nucleotides thereof; and a reverse primer having the sequence GACATGC-CTTTTGGGCCCAGAGGCTAGTGTTAC-CACTAGGGG (SEQ ID NO. 11) or at least 13 contiguous nucleotides thereof.

Preferably the forwards primer comprises at least 15 contiguous nucleotides of SEQ ID NO. 10. Preferably the reverse primer comprises at least 15 contiguous nucleotides of SEQ ID NO. 11.

In a particularly preferred embodiment, the forwards primer has the sequence:

```
GCGGTCCCACTCTTCACAG.     (SEQ ID NO. 12)
```

In a particularly preferred embodiment, the reverse primer has the sequence:

```
GCCCAGAGGCTAGTGTTACCA.   (SEQ ID NO. 9)
```

Preferably the reverse primer used in the PCR and the primer used to reverse transcribe the LV RNA are identical, thereby enabling RT-PCR to be performed on the LV RNA using only 2 primers, preferably the forwards and reverse primers indicated above.

It is particularly preferred that quantitative PCR is performed enabling one to determine the quantity of LV in a sample. Furthermore, by being able to determine the quantity of LV in a sample the progression or regression of a Ljungan viral infection can be determined. This will enable researchers to monitor the effectiveness of treatments.

Quantitative PCR procedures are well known to those skilled in the art. In particular, real time PCR procedures and kinetic PCR procedures.

It is particularly preferred that the PCR procedure performed is a real time PCR procedure using an exonuclease probe (also known as TaqMan Probes). The use of exonuclease probes is described above.

The method of the present invention may be performed on any sample suspected of being infected with LV. Suitable samples include tissue samples and body fluid samples. Particularly preferred samples include muscle tissue samples, especially heart tissue, neural cell samples, especially brain cells, endocrine gland samples such as beta cells of the pancreas, thyroid gland or supra renal gland samples and white blood cells (e.g., the buffy coat). White blood cells is the most preferred sample. RNA can be extracted from such samples using any standard procedure, such as by using the QIAamp viral RNA kit (Qiagen, Hilden, Germany).

In one particularly preferred embodiment of the present invention, there is provide a method for detecting LV in a sample, comprising:
(a) isolating RNA from the sample;
(b) reverse transcribing the RNA to obtain a DNA sequence comprising at least 13 contiguous nucleotides of SEQ ID NO.1; and
(c) performing quantitative PCR using an exonuclease probe.

The present invention also provides a kit for performing the method of the present invention, wherein the kit comprises at least one labelled probe that specifically binds to at least 13 contiguous nucleotides of SEQ ID NO.1.

Preferably the kit of the present invention also comprises primer for amplifying a nucleic acid sequence comprising at least 13 contiguous nucleotides of SEQ ID NO.1 and the necessary reagents for amplifying the nucleic acid sequence. Suitable reagents are well known to those skilled in the art and include buffers, Taq polymerase and deoxynucleotides. The kit may also comprise a primer for reverse transcribing LV RNA so that a DNA sequence is obtained that comprises at least 13 contiguous nucleotides of SEQ ID NO.1 and the necessary reagent for reverse transcribing the RNA. Suitable reagents are well known to those skilled in the art and include buffers, a reverse transcriptase and deoxynucleotides.

BRIEF DESCRIPTION OF THE DRAWINGS

The present invention is now described by reference to the following example with reference to the following Figures.

DETAILED DESCRIPTION OF THE INVENTION

EXAMPLES

Example 1

Study Design and Samples

Figure 1:
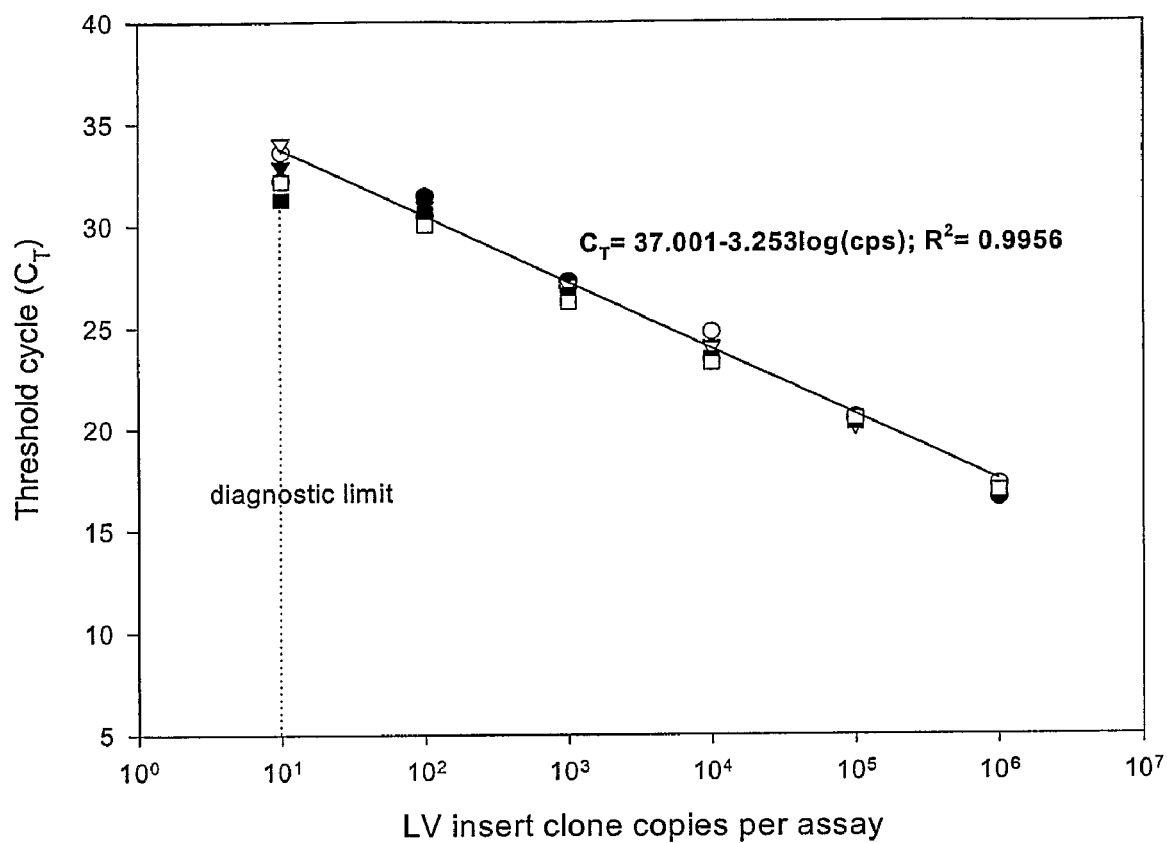
FIG. 1 shows a standard curve for the LV real-time PCR assay. PCR reactions with 1 to $10^6$ copies (cps) of LV insert control plasmid were carried out and the threshold cycle ($C_T$) for each of six replicates per dilution was plotted against the $\log_{10}$ of the corresponding initial template concentration.

LVs were isolated from bank voles in BHK-21 cells from the American Type Culture Collection (ATCC) as described previously (Niklasson et al., Virology, 255, 86-93, 1999). The cell culture supernatants were either passaged on green monkey kidney cells (ATCC) or were injected intracerebrally in 1-day-old suckling mice for propagation. RNA from the LV prototype strain 87-012, prepared from suckling mouse brain (SMB), was used as an external standard PCR control ($TCID_{50}$: $6.2 \times 10^3$) to test the designed real-time RT-PCR assay. A standard curve was generated using 10-fold serial dilutions of an in-house LV insert recombinant plasmid. Specificity tests were performed with viral RNA isolated from stocks of six different LV strains used as positive controls whereas nucleic acids from 19 cell culture supernatants infected with different viruses, two clinical specimens and one DNA standard of other viruses (including the most closely related Human Parechovirus type 1, Encephalomyocarditis virus—EMCV and Theiler's Murine Encephalomyelitis virus—TMEV) were used as negative controls (see Table 2).

The new PCR assay was applied to confirm the presence of LV infection in 60 different tissue samples (collected from brain, liver, lung, kidney, pancreas and heart) from six laboratory mice, which were intraperitoneally infected with LV strain 145SL, and four non-infected mice sacrificed after one week; placenta samples of five laboratory mice, which were infected with LV during pregnancy and showed symptoms of intrauterine death (IUD); six different samples (placenta/umbilicus) of four Swedish patients with pre-eclampsia previously found positive for LV by IHC; and one SMB isolate from pig (SMB 941) previously found LV positive by a semi-nested RT-PCR (all samples were kindly provided by Apodemus AB, Stockholm, Sweden).

Oligonucleotides Design and Synthesis

Primers and minor-groove-binder (MGB) probes were carefully designed. The primer set chosen amplifies a 187-bp fragment in the 5'-untranslated region (5'-UTR) of the LV genome. The following LV nucleotide sequences (with respective NCBI GenBank accession number or other source) were included in the alignment study for the primer and probe design: LV 87-012 (accession no. NC 003976; AF327920), 174F (accession no. AF327921), 145SL (accession no. AF327922), M1146 (accession no. AF538689), and NY64-7855 (unpublished data).

The primers used were 5'-GCGGTCCCACTCTTCA-CAG-3' (SEQ ID NO. 12) (forward, nt 255-274) and 5'-GC-CCAGAGGCTAGTGTTACCA-3' (SEQ ID NO. 9) (reverse, nt 442-424). The amplicon-specific MGB probes were 5'-TGTCCAGAGGTGAAAGC-3' (SEQ ID NO. 7) ($MGB_c$, nt 306-290) and 5'-TGTCGAGAGGTGAAAGC-3' (SEQ ID NO.8) ($MGB_g$, nt 306-290) labelled with the fluorescent reporter dye FAM (6-carboxyfluorescein) at the 5'-end and a dark quencher MGB (minor groove binder) at the 3'-end. Nucleotide positions refer to NCBI sequence GenBank accession no. NC 003976. Primers were obtained from TIB MOLBIOL, Berlin, Germany and probes from Applied Biosystems, Warrington-Cheshire, UK.

RNA Extraction and cDNA Synthesis

RNA from samples could be either isolated by different commercial kits (e.g. Qiagen) or especially for fibrogen tissue samples by Chirgwin's protocol for ultracentrifugation of a guanidinium thiocyanate lysate through a CsCl cushion (Chirgwin et al., Biochemistry, 18, 5294-5299, 1979). Contamination was controlled between homogenization of samples as described previously by Schowengerdt et al., J. Heart Lung Transplant., 15, 111-123, 1996.

To obtain cDNA 5 µl of sample RNA was reverse transcribed in a 10 µl final reaction volume containing 50 mM Tris-HCl (pH 8.3), 75 mM KCl, 3.0 mM $MgCl_2$, 0.125 mM (each) dATP, dCTP, dGTP and dTTP, 10 mM dithiothreitol, 10 U of RNasin (Promega, Mannheim, Germany), 50 U of murine leukaemia virus reverse transcriptase (Invitrogen, Karlsruhe, Germany) and 0.125 µM reverse primer. Cycling parameters were 5 min at 60° C., 20 min at 37° C. and 5 min at 95° C. on a Biometra TRIO thermoblock cycler (Biometra, Göttingen, Germany).

Real-Time PCR.

TaqMan-PCR was carried out in a 96-well microtiter plate format (ABgene, Epsom-Surrey, UK). The PCR mix was made up to a volume of 25 µl containing 2.5 µl of cDNA template, 50 mM Tris-hydrochloride (pH 9), 50 mM KCl, 4 mM $MgCl_2$, 0.2 mM (each) dATP, dCTP, dGTP and dUTP, 0.5 U of uracil-N-glycosylase (UNG) (Invitrogen, Karlsruhe, Germany), 1.25 U of Taq DNA polymerase (Invitrogen, Karlsruhe, Germany), 0.1 µM (each) of the forward and reverse primers, 0.1 µM (each) of the fluorescence-labelled MGB probes and 1.0 µM ROX as a passive reference. After UNG treatment, to avoid amplicon cross-contamination, at 50° C. for 2 min and initial denaturation at 95° C. for 10 min, the DNA was amplified by 35 two-step cycles (15 seconds at 95° C., 30 seconds at 60° C.) on an ABI Prism 7700 Sequence Detector (Applied Biosystems, Foster City, Calif., USA).

Quality of RNA preparation from clinical samples was tested by two reference gene quantitative real-time RT-PCR assays specific for human glyceraldehyde 3-phosphate dehydrogenase (GAPDH) and RNA polymerase II (RPII) as described previously by Radonic et al., Biochem. Biophys. Res. Commun., 313, 856-862, 2004.

Generation of an In-House LV Insert Control Plasmid.

Taq polymerase amplified PCR product of the external standard PCR control from LV 87-012 was checked by agarose gel electrophoresis. The single, discrete 187-bp band was excised from the agarose gel and extracted with the QIAquick gel extraction kit (Qiagen, Hilden, Germany) according to the manufacturer's instructions.

Extracted PCR product was cloned into a vector plasmid and propagated into transformed E. coli cells with the pcDNA3.1/V5-His-TOPO TA Expression kit according to the manufacturer's instructions (Invitrogen, Karlsruhe, Germany). Insert control of the 187-bp fragment was done with the T7 and BGH reverse sequencing primers. Plasmids with the LV insert were isolated from positive E. coli colonies with the QIAGEN Plasmid Mini kit (Qiagen, Hilden, Germany) according to the manufacturer's instructions.

Sequence Analysis.

Amplicons were purified using the QIAquick gel extraction kit (Qiagen, Hilden, Germany) and were directly sequenced with the Big Dye terminator cycle sequencing kit (Applied Biosystems, Warrington-Cheshire, UK) on a 377 DNA automated sequencer (Applied Biosystems, Foster City, Calif., USA) and analyzed with NCBI BLAST software (www.ncbi.nlm.nih.gov/BLAST/).

Results

Ten-fold dilutions, six replicates per dilution, of our in-house LV insert plasmid were used to generate a standard curve plotting threshold cycle value ($C_T$) against dilution (FIG. 1). The representative standard curve demonstrates a high linear correlation in the real-time PCR assay over six orders of magnitude, 1 to $10^6$ copies/assay, with a detection limit of 10 copies ($R^2$=0.9956). Intra-assay precision was assessed by one operator processing three virus-positive control preparations of the in-house LV insert plasmid ($10^1$, $10^2$ and $10^3$ copies/assay) six times in one experiment (three series) and inter-assay precision by processing the same controls six times in three different experiments carried out by different operators (each one series). The mean $C_T$ values and standard deviation (SD) for each assay are compared in Table 1 indicating that the results were very reproducible.

The specificity of the method was evaluated using RNA purified from six different LV strains as positive controls and further nucleic acids from 22 different virus samples as negative controls. All LV cDNA samples were positive in the PCR and amplicons could be isolated for sequence analysis, whereas none of the negative controls contributed to a false-positive signal in the real-time PCR analysis (Table 2). The positive PCR results could be confirmed by sequence analysis of the PCR products and could be distinguished into "Swedish" and "non-Swedish" LV strains (data not shown).

The new quantitative real-time RT-PCR assay was applied to confirm the presence of LV infection in different sample types from both rodents and humans. 33 of 36 (92%) tissue samples collected from different organs of six laboratory mice, which were intraperitoneally infected with the LV strain 145SL and sacrificed after one week, were LV positive in the PCR-screening. High viral loads could be found in the brain tissue samples with up to 107 viral copies per mg tissue with respect to the initial sample weight, while none of four non-infected laboratory mice was positive in any of the tested organs (data not shown). Furthermore, in all placenta samples of five laboratory mice, which were LV-infected during pregnancy and showed symptoms of IUD, LV genome sequences could be detected by the new method presenting viral loads between $2.4 \times 10^3$ and $5.0 \times 10^6$ viral copies per mg tissue, mean: $1.8 \times 10^6$ copies (data not shown). Moreover, in two of six (33%) placenta/umbilicus samples from four Swedish patients with pre-eclampsia, previously found positive for LV by IHC, and in one pig isolate (SMB 941), previously found LV positive by semi-nested RT-PCR, LV genome sequences could be confirmed by the established real-time RT-PCR (Table 3). In comparison, the viral load in the LV external standard PCR control of LV 87-012 (see Table 2) used in all tests was 70 times higher than in these weak positive samples. Nevertheless, the positive PCR results could be confirmed by sequence analysis of the PCR products with more than 98% sequence homology to LV prototype strain 87-012 (data not shown).

Discussion

As LV is considered a causative agent of human diseases carried by rodents there is a need for a reliable and sensitive assay for detecting the virus in different kinds of tissue or fluids from both animals and humans.

Three Tasks were Essential for the Design of the 5'-UTR-PCR-Assay Presented Here:
1. find an appropriate/conserved target sequence in the 5'-UTR which is specific for all strains of LV, but which excludes the detection of other possible types of picornaviruses;
2. detect all known Swedish and American strains of LV and also divergent strains at the same time in one assay; and
3. quantify even low virus load of LV genomes in different types of samples from both animals and human patients.

Upon the basis of sequence data for five of seven known LV strains the inventors developed a new quantitative real-time RT-PCR assay, which includes two MGB probes specific to the conserved 5'-UTR able to detect exclusively all known LV strains, considering a polymorphism on nucleotide-position 302, with guanine standing for the Swedish LV strains and cytosine for the American LV strains (refer to NCBI sequence GenBank accession no. NC 003976). Due to only short stretches of conserved DNA in the target sequence the inventors decided to use MGB-probes (17 mers) instead of a conventional TaqMan®-probe (approximately 20-30 mers) for the detection of LV-specific nucleic acids. MGB technology facilitates a precise detection of the fluorescent reporter dye, because the used probes have a non-fluorescent quencher at the 3'-end. Furthermore, the minor-groove-binder increases the melting temperature of a probe making it possible to design shorter probes and therefore avoiding the risk of mismatches to their target sequences (Kutyavin et al., Nucleic Acids Res., 28, 655-661, 2000). To detect all known and other divergent LV strains in one assay the inventors applied two different MGB-conjugated fluorogenic DNA probes, considering a polymorphism on nucleotide-position 24 in SEQ ID NO. 1 in the aligned LV genomic sequences either with guanine or cytosine. The simultaneously application of two different MGB probes specific for a single base polymorphism and conjugated with the same fluorescent reporter dye is considered to be novel. Based on their calculation for primer and probe design, the chosen target sequence and the established assay represent the optimal application for screening of 5'-UTR-specific sequences of LV with the demands mentioned above. Other alternatives by using other regions inside the 5'-UTR will lead to difficulties especially in positioning the probe.

The new assay has a high sensitivity with a detection limit of 10 viral copies/assay and allows reliable quantification of LV RNA over six orders of magnitude, directly isolated from sample material. None of the LV negative controls (including the most closely related Human Parechovirus type 1, EMCV and TMEV) was detected positive in the specificity tests. The high specificity of the assay is ensured both by the primers and probes selected for the real-time PCR and by the specific primer used to initiate cDNA synthesis. In addition, the results for intra- and inter-assay precision indicate that the assay is highly reproducible.

The assay was tested with different laboratory and clinical samples from both rodents and humans resulting in high detection scores for LV genome sequences. Two of six human placenta/umbilicus probes, previously found positive for LV by IHC, and one SMB isolate from pig, previously found LV positive by a semi-nested RT-PCR, were also detected weak positive by the new assay and could be confirmed by sequence analysis as LV-related.

Only 33% of the immunohistologically pre-tested placenta/umbilicus samples could be confirmed by this sensitive viral nucleic acid detection technique, suggesting that conventional detection methods like viral antigen detection by IHC may result in some false-positive results due to cross-reactions with other picornaviruses, which is generally a common problem for this method. Other current tests like e.g. virus isolation and detection of CPE are very laborious and do not detect LVs effectively (Johansson et al., Biochem. Biophys. Res. Commun., 317, 1023-1029, 2004). However, the results in this study showed that the quantitative real-time RT-PCR can be applied for different types of samples even with low LV RNA load.

In conclusion, the results show that identification of LV in human diseases can be achieved. As seen in several zoonotic diseases humans are often dead-end hosts and it may be easier to isolate the etiologic agent from the reservoir or vector than from the patient. Also, because of the time elapsed between primary infection and onset of disease, the infectious agent may be present only in very small amounts or absent. However, as shown here, the application of the method of the present invention can be used to detect even small amounts of viral nucleic acid in different kinds of tissue and fluids, and it will help, besides serological analysis and IHC, to elucidate the role of LV as a human pathogen for numerous diseases. The identification of LV in large amounts of environmental samples from different rodent populations and clinical samples should lead to a more precise picture about the distribution of LV in several geographical regions and should help to calculate the resulting risk for the human population.

Example 2

Out bred CD1 mice (CD-1 (ICR) Br Charles River laboratories, Germany) were infected intraperitoneally with LV strain 145SL (GenBank acc. no. AF327922) with approximately 1000 $ID_{50}$ one day postnatal. Animals were kept at the Astrid Fagraeus Laboratory, Swedish Institute for Infectious Disease Control, Stockholm, Sweden and were sacrificed at different time points post infection. Organs were taken and frozen (first part) or immediately placed in RNAlater® buffer (Ambion, USA) (second part) respectively. The tissues were shipped to the Robert Koch-Institute, Berlin, Germany for PCR analysis. RNA extraction was performed as described above. Extracted RNA was reverse transcribed and virus load was determined as described above. To verify the extraction procedure all organs were tested for hypoxanthine phosphoribosyltransferase (HPRT) mRNA as a house keeping gene by reverse transcription and TaqMan® PCR (TibMolBiol, Berlin, Germany). All organs tested positive for HPRT mRNA.

Figure 2:
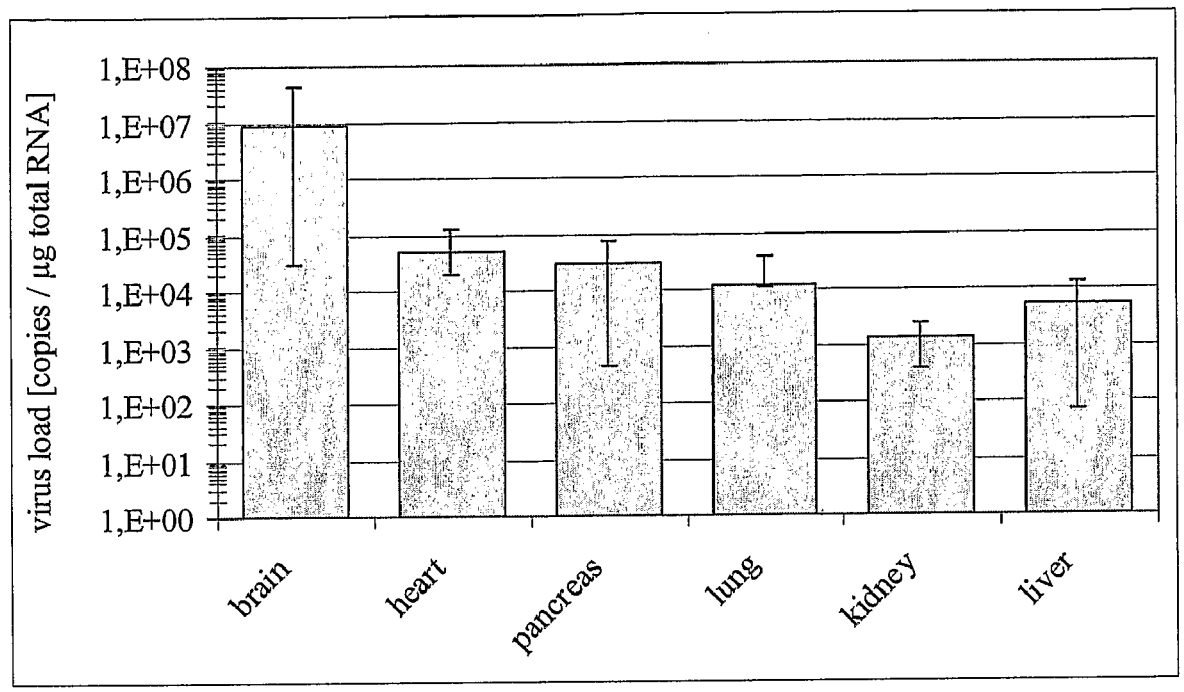
FIG. 2 shows Ljungan Virus (LV) RNA in different mouse organs (brain, heart, liver: n=6; pancreas, lung: n=5; kidney: n=4) from LV infected mice 6 days post infection; virus load was normalized to 1 µg extracted total RNA yield (means and standard errors of the means). Virus positive strand RNA was determined by RT-TaqMan® PCR as described herein.

In the first part of the study six infected mice of unknown gender were sacrificed six days post infection (dpi) and all had clinical signs of encephalitis. Brain, heart, pancreas, lung, kidney and liver were analysed by histology and PCR. Histological observations showed tissue damage in brain. Highest virus load was found in brain ($10^7$ copies/µg total RNA) followed by heart and pancreas (approximately $10^{4.5}$ copies/µg total RNA). In lung and liver approximately $10^4$ virus copies/µg total RNA could be detected. The lowest virus load was found in the kidney ($10^3$ copies) (FIG. 2).

All organs from four non infected control mice were all negative for LV.

During this study we have gained evidence from laboratory observations that gender and stress could play an important role for the outcome of LV infection in laboratory mice as well as in bank voles. In contrast to the first part of the study where gender and stress were not considered as important factors, in the second part only male mice were included and kept under stress. Therefore three to four animals were kept together from day 25 on. Two to four mice were sacrificed at different time points and brain, heart, pancreas, lung, kidney, liver, spleen and faeces were analysed for virus RNA as described before (13 dpi: n=4; 17, 27, 56, 98, 130 and 174 dpi: n=4). Bladder and thymus samples were collected when possible.

In the acute phase of infection the animals had clinical symptoms of encephalitis again with the same histological picture. Animals who survived the encephalitis (mortality rate approximately 30%) developed diabetes.

Figure 3:
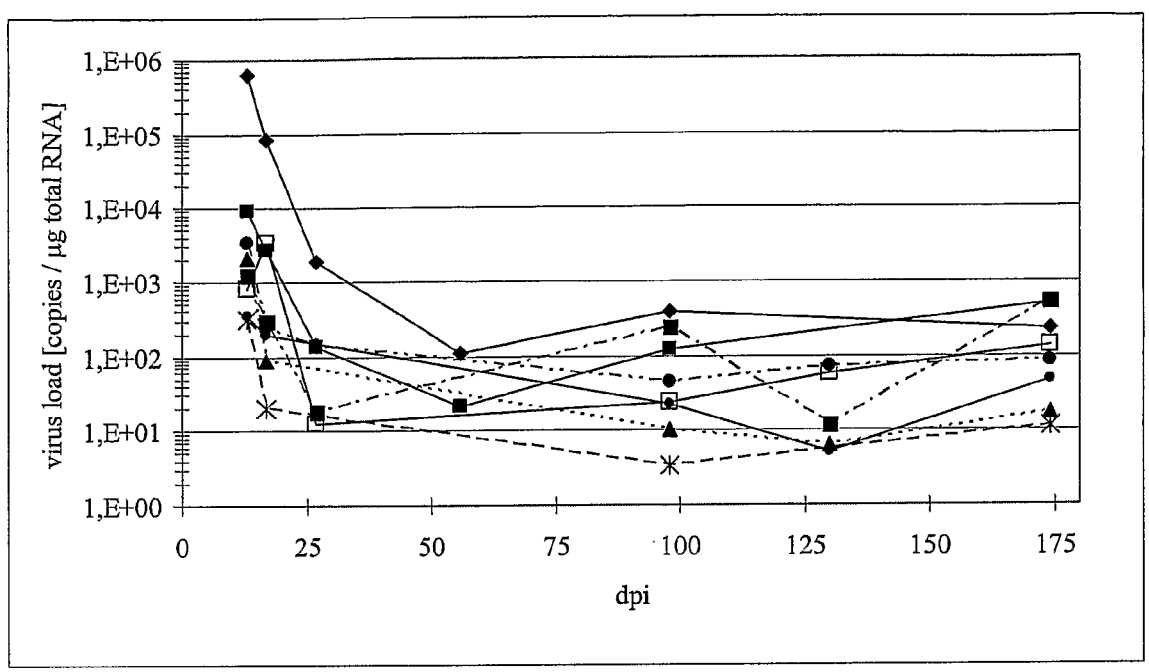
FIG. 3 shows Ljungan Virus (LV) RNA in different organs (after 13 dpi: brain, heart, lung, liver n=4; pancreas, kidney, spleen, faeces n=3; other time points n=2 for all organs) from LV infected male laboratory mice exposed to stress; virus load was normalized to 1 µg extracted total RNA yield (means, no standard error bars for clarity of the figure). Virus positive strand RNA was determined by RT-TaqMan® PCR as described herein.

All investigated organs were tested positive for LV with similar virus loads in the acute phase of infection as in the first study. Highest virus copies were found in brain ($10^6$ copies/µg total RNA 13 dpi) followed by heart ($10^4$ copies/µg total RNA 13 dpi) again. Lowest virus copies were found in liver and kidney (ca. $5 \times 10^2$ copies/µg total RNA 13 dpi). In the course of time the virus load decreased and persisted at a low level ($10$-$10^3$ copies/µg total RNA) in all organs (FIG. 3). In thymuses virus load was low in comparison with the other organs (200 copies/µg total RNA 13 dpi and 3 copies/µg total RNA 56 dpi respectively). Bladder could be removed from older animals (98 and 130 dpi respectively). The detected virus load in these organs was 300 copies/µg total RNA (98 dpi) and 90 copies/µg total RNA (130 dpi) respectively.

The present study shows that LV infection in laboratory mice can be detected using PCR.

Example 3

The inventors have detected LV in white blood cell samples obtained from children with recent onset of type 1 diabetes (8 out of 8 tested positive) using the PCR method described above. LV was also detected in 12 out of 12 patients with multiple sclerosis. In control patients, LV was found in 1 out of 30 patients tested. All specimens were white blood cell samples. The LV positive PCR results have been verified by sequence analysis of the PCR product.

All documents cited above are incorporated herein by reference.

TABLE 1

Intra-assay and inter-assay precision of the LV real-time PCR

| $Log_{10}$ virus control dilution per assay | Intra-assay* | | Inter-assay† | |
|---|---|---|---|---|
| | Mean $C_T$ | SD | Mean $C_T$ | SD |
| $10^1$ | 32.71 | 1.02 | 31.89 | 1.42 |
| $10^2$ | 30.66 | 0.51 | 29.95 | 1.27 |
| $10^3$ | 26.89 | 0.39 | 26.82 | 0.29 |

*Each dilution of LV insert clone was tested six times in three series by one operator (n = 18).
†Each dilution of LV insert clone was tested six times in one series by three operators (n = 18).
$C_T$: Threshold cycle value.

TABLE 2

Overview of the results obtained in the specificity tests for the LV real-time PCR*

| Virus sample | RT-PCR | Mean $C_T$ | SD | Viral load (cps per assay) | Sequence |
|---|---|---|---|---|---|
| LV 87-012† | + | 26.32 | 0.29 | $1.9 \times 10^3$ | + |
| LV 174F‡ | + | 14.40 | 0.23 | $8.8 \times 10^6$ | + |
| LV 145SL‡ | + | 15.05 | 0.27 | $5.6 \times 10^6$ | + |
| M-1146‡ | + | 20.87 | 0.34 | $9.1 \times 10^4$ | + |
| NY64-7855‡ | + | 27.61 | 0.21 | $7.7 \times 10^2$ | + |
| NY64-7947‡ | + | 28.87 | 0.15 | $3.2 \times 10^2$ | + |
| Echovirus type 30 (00-58/1 Rostock)§ | − | 35.00 | 0 | − | nd |
| Human Parechovirus type 1† | − | 35.00 | 0 | − | nd |
| EMCV (76/5167)¶ | − | 35.00 | 0 | − | nd |
| EMCV (Creighead)¶ | − | 35.00 | 0 | − | nd |
| EMCV (M)# | − | 35.00 | 0 | − | nd |
| TMEV (995 OH)# | − | 35.00 | 0 | − | nd |
| TMEV (57 OH)# | − | 35.00 | 0 | − | nd |
| ADV serotype 2$ | − | 35.00 | 0 | − | nd |
| ADV serotype 3$ | − | 35.00 | 0 | − | nd |
| ADV serotype 4$ | − | 35.00 | 0 | − | nd |
| ADV serotype 5$ | − | 35.00 | 0 | − | nd |
| ADV serotype 9$ | − | 34.91 | 0.13 | − | nd |
| ADV serotype 12$ | − | 34.78 | 0.32 | − | nd |
| ADV serotype 40⁺ | − | 35.00 | 0 | − | nd |

TABLE 2-continued

Overview of the results obtained in the specificity tests for the LV real-time PCR*

| Virus sample | RT-PCR | Mean $C_T$ | SD | Viral load (cps per assay) | Sequence |
| --- | --- | --- | --- | --- | --- |
| Human cytomegalovirus (AD-169)[£] | − | 34.78 | 0.32 | − | nd |
| Influenza virus A (Moscow)[θ] | − | 35.00 | 0 | − | nd |
| Influenza virus B (Hong-Kong)[θ] | − | 33.89 | 1.58 | − | nd |
| Hantaan virus (76-118)[¶] | − | 35.00 | 0 | − | nd |
| Dobrava virus (Slovenia)[¶] | − | 34.56 | 0.63 | − | nd |
| Puumala virus (Sotkamo)[¶] | − | 34.64 | 0.51 | − | nd |
| Seoul virus (80-39)[¶] | − | 34.71 | 0.41 | − | nd |
| Parvovirus B19 (99/800, NIBSC) | − | 35.00 | 0 | − | nd |
| LV 87-012 external standard PCR control | + | 26.06 | 0.07 | $2.3 \times 10^3$ | + |

*Each sample was tested in duplicate (n = 2). '+' = positive result; '−' = not found; 'nd' = not done.
$C_T$: Threshold cycle value; cps: number of copies; EMCV: Encephalomyocarditis virus; TMEV: Theiler's Murine Encephalomyelitis virus; ADV: Human Adenovirus.
Cultured in:
[†]GMK monkey kidney cells (ATCC);
[‡]10% SMB culture;
[§]RD human muscle cells (ATCC);
[¶]Vero E6 monkey kidney cells (ATCC);
[#]BHK-21 hamster kidney cells (ATCC);
[$]Hep-2 human liver cells (ATCC);
[◊]Graham human kidney cells (ATCC);
[£]Fi301 human lung fibroblasts (Institute of Virology, Charité, Berlin, Germany),
[θ]Isolated from throat swab specimen.

TABLE 3

Overview of the results obtained for pre-tested clinical samples and virus isolate*

| Sample | RT-PCR | Mean $C_T$ | SD | Viral load (cps per mg tissue) | Sequence |
| --- | --- | --- | --- | --- | --- |
| placenta sample/patient A | + | 32.38 | 0.26 | $5 \times 10^1$ | + |
| placenta sample/patient E | + | 31.89 | 1.28 | $5 \times 10^1$ | + |
| virus isolate SMB 941 | + | 32.36 | 0.89 | $3 \times 10^1$ | + |

*Each sample was tested in duplicate (n = 2). '+' = positive result.
$C_T$: Threshold cycle value; cps: number of copies.

---

The invention claimed is:

1. A method for detecting Ljungan virus (LV) comprising detecting a nucleic acid sequence comprising at least 13 contiguous nucleotides of the sequence:CTGCRYAGGTG-GCTTTCACCTCTSGACAGYGC (SEQ ID NO. 1) or the reverse complement sequence, wherein the nucleic acid sequence is detected by using at least one probe that specifically hybridizes to at least 13 contiguous nucleotides of SEQ ID NO. 1 or the reverse complement sequence.

2. The method according to claim 1, wherein the nucleic acid sequence to be detected is an RNA sequence.

3. The method according to claim 1, wherein the nucleic acid sequence to be detected is a DNA sequence.

4. The method according to claim 1, comprising the initial step of reverse transcribing LV RNA into cDNA.

5. The method according to claim 1, wherein the nucleic acid sequence being detected comprises at least 15 contiguous nucleotides of SEQ ID NO. 1 or the reverse complement sequence.

6. The method according to claim 1, wherein the nucleic acid sequence being detected comprises at least 17 contiguous nucleotides of SEQ ID NO. 1 or the reverse complement sequence.

7. The method according to claim 1, wherein the nucleic acid sequence being detected comprises the following sequence:GCTTTCACCTCTSGACA (SEQ ID NO. 3) or the reverse complement sequence.

8. The method of claim 1, wherein the probe is less than 25 nucleotides in length.

9. The method of claim 1, wherein the probe is 17 nucleotides or less in length.

10. The method according to claim 1, wherein the probe binds in the minor groove of the nucleic acid being detected.

11. The method according to claim 1, wherein the probe is a single stranded DNA probe.

12. The method according to claim 1, wherein the probe is an exonuclease probe.

13. The method according to claim 4, wherein a DNA primer is annealed to the RNA sequence at a position enabling the production of a DNA sequence comprising at least 13 contiguous nucleotides of SEQ ID NO. 1 and the primer extended by the action of a reverse transcriptase.

14. The method of claim 13, wherein the primer has the sequence

GCCGAGAGGCTAGTGTTACCA.        (SEQ ID NO. 9)

15. The method of claim 1 comprising:
(a) reverse transcribing Ljungan virus (LV) RNA so that a DNA sequence is obtained that comprises at least 13 contiguous nucleotides of SEQ ID NO. 1;
(b) amplifying the DNA sequence; and
(c) detecting the presence of the amplified DNA sequence, wherein the nucleic acid sequence is detected by using at least one probe that specifically hybridizes to at least 13 contiguous nucleotides of SEQ ID NO. 1 or the reverse complement sequence.

16. The method of claim 15, wherein the DNA sequence is amplified by the polymerase chain reaction (PCR).

17. The method of claim 16, wherein the primers used in the PCR reaction amplify a DNA sequence comprising at least 13 contiguous nucleotides of SEQ ID NO.1.

18. The method of claim 17, wherein the primers comprise: a forwards primer having the sequence TAGGGGCTG-TACCCGGGCGGTCCCACTCTTCACAG (SEQ ID NO. 10) or at least 13 contiguous nucleotides thereof; and a reverse primer having the sequence CCCCTAGTGGTAACACTAGCCTCTGGGC-CCAAAAGGCATGTC (SEQ ID NO. 11) or at least 13 contiguous nucleotides thereof.

19. The method of claim 18, wherein the forwards primer has the sequence:

GCGGTCCCACTCTTCACAG.        (SEQ ID NO. 12)

20. The method of claim 18, wherein the reverse primer has the sequence:

GCCCAGAGGCTAGTGTTACCA        (SEQ ID NO. 9).

21. The method of claim 16, wherein quantitative PCR is performed.

22. The method of claim 16, wherein the PCR procedure performed is a real time PCR procedure and an exonuclease probe is used to detect the amplified DNA sequence.

23. The method of claim 1, wherein the Ljungan virus is detected in a tissue sample or a body fluid sample.

24. The method of claim 23, wherein the sample is a muscle tissue sample, a neural cell sample, endocrine gland samples or a white blood cell sample.

25. A kit for performing the method of claim 1, wherein the kit comprises at least one probe that specifically binds to at least 13 contiguous nucleotides of SEQ ID NO.1 and has a complementary sequence to at least 13 contiguous nucleotides of SEQ ID NO. 1.

26. The kit of claim 25, which additionally comprises primers for amplifying a nucleic acid sequence comprising at least 13 contiguous nucleotides of SEQ ID NO.1 and the necessary reagents for amplifying the nucleic acid sequence.

27. The kit of claim 25, which additionally comprises a primer for reverse transcribing Ljungan virus RNA so that a DNA sequence is obtained that comprises at least 13 contiguous nucleotides of SEQ ID NO.1 and the necessary reagent for reverse transcribing the RNA.

* * * * *

SEQUENCE LISTING

<160> NUMBER OF SEQ ID NOS: 12

<210> SEQ ID NO 1
<211> LENGTH: 32
<212> TYPE: DNA
<213> ORGANISM: Ljungan virus

<400> SEQUENCE: 1
ctgcryaggt ggctttcacc tctsgacagy gc          32

<210> SEQ ID NO 2
<211> LENGTH: 32
<212> TYPE: DNA
<213> ORGANISM: Ljungan virus

<400> SEQUENCE: 2
gcrctgtcsa gaggtgaaag ccacctrygc ag          32

<210> SEQ ID NO 3
<211> LENGTH: 17
<212> TYPE: DNA
<213> ORGANISM: Ljungan virus

<400> SEQUENCE: 3

```
gctttcacct ctsgaca                                                    17

<210> SEQ ID NO 4
<211> LENGTH: 17
<212> TYPE: DNA
<213> ORGANISM: Ljungan virus

<400> SEQUENCE: 4
tgtcsagagg tgaaagc                                                    17

<210> SEQ ID NO 5
<211> LENGTH: 17
<212> TYPE: DNA
<213> ORGANISM: Ljungan virus

<400> SEQUENCE: 5
gctttcacct ctggaca                                                    17

<210> SEQ ID NO 6
<211> LENGTH: 17
<212> TYPE: DNA
<213> ORGANISM: Ljungan virus

<400> SEQUENCE: 6
gctttcacct ctcgaca                                                    17

<210> SEQ ID NO 7
<211> LENGTH: 17
<212> TYPE: DNA
<213> ORGANISM: Artificial Sequence
<220> FEATURE:
<223> OTHER INFORMATION: probe sequence

<400> SEQUENCE: 7
tgtccagagg tgaaagc                                                    17

<210> SEQ ID NO 8
<211> LENGTH: 17
<212> TYPE: DNA
<213> ORGANISM: Artificial Sequence
<220> FEATURE:
<223> OTHER INFORMATION: probe sequence

<400> SEQUENCE: 8
tgtcgagagg tgaaagc                                                    17

<210> SEQ ID NO 9
<211> LENGTH: 21
<212> TYPE: DNA
<213> ORGANISM: Artificial Sequence
<220> FEATURE:
<223> OTHER INFORMATION: primer sequence

<400> SEQUENCE: 9
gcccagaggc tagtgttacc a                                               21

<210> SEQ ID NO 10
<211> LENGTH: 35
<212> TYPE: DNA
<213> ORGANISM: Artificial Sequence
<220> FEATURE:
<223> OTHER INFORMATION: primer sequence

<400> SEQUENCE: 10
```

-continued

```
tagggctgt acccgggcgg tcccactctt cacag        35
```

<210> SEQ ID NO 11
<211> LENGTH: 42
<212> TYPE: DNA
<213> ORGANISM: Artificial Sequence
<220> FEATURE:
<223> OTHER INFORMATION: primer sequence

<400> SEQUENCE: 11

```
gacatgcctt tgggcccag aggctagtgt taccactagg gg        42
```

<210> SEQ ID NO 12
<211> LENGTH: 19
<212> TYPE: DNA
<213> ORGANISM: Artificial Sequence
<220> FEATURE:
<223> OTHER INFORMATION: primer sequence

<400> SEQUENCE: 12

```
gcggtcccac tcttcacag        19
```